(12) United States Patent
Hill et al.

(10) Patent No.: US 10,441,190 B2
(45) Date of Patent: Oct. 15, 2019

(54) SYSTEMS AND METHODS FOR PROVIDING A WAKING MECHANISM

(71) Applicant: NodStop, LLC, Provo, UT (US)

(72) Inventors: Nathaneal Hill, Provo, UT (US); Jonathan Miller, Provo, UT (US); Loren Adams, Provo, UT (US); Logan Teancum Kratzer, Orem, UT (US)

(*) Notice: Subject to any disclaimer, the term of this patent is extended or adjusted under 35 U.S.C. 154(b) by 401 days.

(21) Appl. No.: 14/518,343

(22) Filed: Oct. 20, 2014

(65) Prior Publication Data

US 2015/0282731 A1 Oct. 8, 2015

(51) Int. Cl.
*A61B 5/04* (2006.01)
*A61B 5/0482* (2006.01)
(Continued)

(52) U.S. Cl.
CPC .......... *A61B 5/0482* (2013.01); *A61B 5/048* (2013.01); *A61B 5/04012* (2013.01); *A61B 5/0478* (2013.01); *A61B 5/18* (2013.01); *A61B 5/4809* (2013.01); *A61B 5/4812* (2013.01); *A61B 5/6803* (2013.01); *A61B 5/6814* (2013.01); *A61B 5/742* (2013.01); *A61B 5/7405* (2013.01); *A61B 5/7455* (2013.01); *A61M 21/00* (2013.01); *A61M 2021/0022* (2013.01); *A61M 2021/0027* (2013.01); *A61M 2021/0044* (2013.01);
(Continued)

(58) Field of Classification Search
CPC ........... A61B 5/0482; A61B 5/7405; A61B 5/04012–04018; A61B 5/7455; A61B 5/18; A61B 5/742; A61B 5/6814; A61B 5/4809; A61B 5/4812; A61B 5/0478; A61B 5/048; A61B 5/6803; A61M 21/00; A61M 2021/0044; A61M 2021/0027; A61M 2021/0022; A61M 2230/10; A61M 2205/50; A61M 2205/8206
See application file for complete search history.

(56) References Cited

U.S. PATENT DOCUMENTS

| 4,967,038 A * | 10/1990 | Gevins | ................. | A61B 5/0017 |
|---|---|---|---|---|
| | | | | 600/383 |
| 2004/0010203 A1* | 1/2004 | Bibian | .................. | A61B 5/048 |
| | | | | 600/544 |

(Continued)

FOREIGN PATENT DOCUMENTS

WO 2012-170816 12/2012

*Primary Examiner* — Navin Natnithithadha
*Assistant Examiner* — Andrey Shostak
(74) *Attorney, Agent, or Firm* — Dax D. Anderson; Kirton & McConkie

(57) ABSTRACT

An EEG monitor with sensors placed to detect signals and analyze the signals to determine if a frequency below 12 Hz, and more particularly between 3 Hz and 8 Hz, called theta waves, are present. Theta waves are generated when the brain is entering a drowsy or sleep mode. The sensors detect brain wave signals and transmit the signals to a microprocessor which analyzes the signals and determines the brain waves being detected. The brain waves are continuously monitored and the data is continuously transmitted to a microprocessor. If brain waves are detected in the predetermined range of between 3 Hz and 8 Hz the microprocessor activates a stimulus, to wake up the person wearing the device. The stimulus may be visual, auditory or tactile, such as an actuator, a phone call or any other stimulus.

13 Claims, 7 Drawing Sheets

(51) Int. Cl.
*A61M 21/00* (2006.01)
*A61B 5/0478* (2006.01)
*A61B 5/048* (2006.01)
*A61B 5/00* (2006.01)
*A61B 5/18* (2006.01)

(52) U.S. Cl.
CPC . *A61M 2205/50* (2013.01); *A61M 2205/8206* (2013.01); *A61M 2230/10* (2013.01)

(56) References Cited

U.S. PATENT DOCUMENTS

| | | | | |
|---|---|---|---|---|
| 2007/0161875 A1* | 7/2007 | Epley | ............... | A61B 5/0484 600/301 |
| 2008/0177197 A1* | 7/2008 | Lee | ............... | A61B 5/165 600/545 |
| 2009/0156956 A1 | 6/2009 | Milgramm et al. | | |
| 2009/0192556 A1 | 7/2009 | Wu et al. | | |
| 2010/0066533 A1* | 3/2010 | Trefz | ............... | A61M 21/00 340/540 |
| 2010/0069775 A1* | 3/2010 | Milgramm | ............... | A61B 5/048 600/544 |
| 2010/0094156 A1* | 4/2010 | Collura | ............... | A61B 5/0482 600/545 |
| 2010/0317931 A1* | 12/2010 | Sarkela | ............... | G16H 15/00 600/301 |
| 2012/0157873 A1 | 6/2012 | Liang et al. | | |
| 2013/0303828 A1* | 11/2013 | Hargrove | ............... | A61N 1/36014 600/13 |
| 2014/0316230 A1* | 10/2014 | Denison | ............... | A61B 5/04012 600/383 |
| 2014/0371833 A1* | 12/2014 | Ghosh | ............... | A61B 19/5225 607/129 |
| 2015/0032021 A1* | 1/2015 | Chen | ............... | A61B 5/7275 600/544 |
| 2016/0220817 A1* | 8/2016 | Xia | ............... | A61N 1/36025 |

* cited by examiner

SYSTEMS AND METHODS FOR PROVIDING A WAKING MECHANISM

BACKGROUND

1. Field of the Invention

The present invention relates generally to detecting brain waves, analyzing those brain waves and applying a stimulus, or waking mechanism, when the detected brain waves are within a predetermined range, and, more particularly, to an apparatus to detect the early stages of sleep in a person applying a stimulus to wake the person up.

2. Background of the Invention and Related Art

Research shows that the human brain emits brain waves which correspond with certain activities. Using an electroencephalogram ("EEG"), researchers have observed brain wave activity in a variety of frequencies which correspond to the brain's activity state. EEGs have been used in the medical industry for monitoring brain wave activity. For example, Beta waves comprise 16-31 Hz, Alpha waves comprise 8-15 Hz, Theta waves comprise 4-7 Hz, and Delta waves comprise 0.1-3 Hz.

EEGs have been used in the medical industry for monitoring brain wave activity but have just recently entered the consumer industry. With the invention of the EEG dry sensor, a wearable device that senses brain waves was made possible. The technology has been used in devices that integrate with software to perform various functions. However, the specific application of providing a user with a constant state of alertness has never been actualized.

Researchers generally measure beta waves and alpha waves in people who are awake and alert. Beta waves are have a high frequency and low amplitude and exhibit an inconsistent pattern and correspond with day to day activities when a person is alert and awake. Beta waves are exhibited when a person is fully awake and when higher functions such as logic and critical reasoning occur.

However, as a person relaxes, the brain begins to exhibit alpha waves, which are characterized by increased amplitude and synchronicity. These brain waves correlate with peaceful meditation.

The brain emits Theta waves as a person transitions from a wakeful state in the alpha and beta ranges to a sleep state. Theta waves further decrease in frequency and further increase in amplitude. A person who emits Theta waves as they pass from a calm relaxed state into a drowsy, but still awake state and transitions to a drowsy and fully asleep state.

Finally, Delta waves are exhibited by a person who is in a deep sleep.

The body and brain have anatomical structures which control sleep. The thalamus is brain structure responsible for consciousness. The thalamus has multiple functions. It may be thought of as a kind of switchboard of information. It is generally believed to act as a relay between different subcortical areas and the cerebral cortex. In particular, every sensory system (with the exception of the olfactory system) includes a thalamic nucleus that receives sensory signals and sends them to the associated primary cortical area. For the visual system, for example, inputs from the retina are sent to the lateral geniculate nucleus of the thalamus, which in turn projects to the visual cortex in the occipital lobe. The thalamus is believed to both process sensory information as well as relay it—each of the primary sensory relay areas receives strong feedback connections from the cerebral cortex. Similarly the medial geniculate nucleus acts as a key auditory relay between the inferior colliculus of the midbrain and the primary auditory cortex, and the ventral posterior nucleus is a key somatosensory relay, which sends touch and proprioceptive information to the primary somatosensory cortex.

The thalamus also plays an important role in regulating states of sleep and wakefulness. Thalamic nuclei have strong reciprocal connections with the cerebral cortex, forming thalamo-cortico-thalamic circuits that are believed to be involved with consciousness. The thalamus plays a major role in regulating arousal, the level of awareness, and activity. Damage to the thalamus can lead to permanent coma.

While sleep is critical to maintaining health, certain activities, such as standing guard, operating a motor vehicle or even studying cannot be properly performed while asleep or even drowsy. An estimated 20% of fatalities on the road are drowsiness related. Currently, waking mechanisms that claim to sense drowsiness do so by using motion sensors. People need something to keep them awake while driving, working, monitoring, etc.

SUMMARY

Systems and methods of monitoring brain wave activity and triggering stimuli waking mechanism based on the measured brain wave activity is disclosed. Some embodiments claim a plurality of EEG contact sensors coupled to a logic circuit. The contacts detect brain wave signals which are analyzed by the logic circuit, and when the signals are within a pre-determined range stimuli are applied. Alternatively, a method is disclosed for arousing a person who is transitioning from an alert state to a sleep state by monitoring the brain waves, and when brain waves between 3 Hz and 8 Hz are detected activating stimuli to arouse the person to a wakeful state. The device can be integrated into any style of headwear piece according to the user's style preference.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

DETAILED DESCRIPTION OF THE PREFERRED EMBODIMENTS

It will be readily understood that the components of the present invention, as generally described and illustrated in the figures herein, could be arranged and designed in a wide variety of different configurations. Thus, the following more detailed description of the embodiments of the system and method of the present invention is not intended to limit the scope of the invention, as claimed, but is merely representative of the presently preferred embodiments of the invention.

Figure 1:
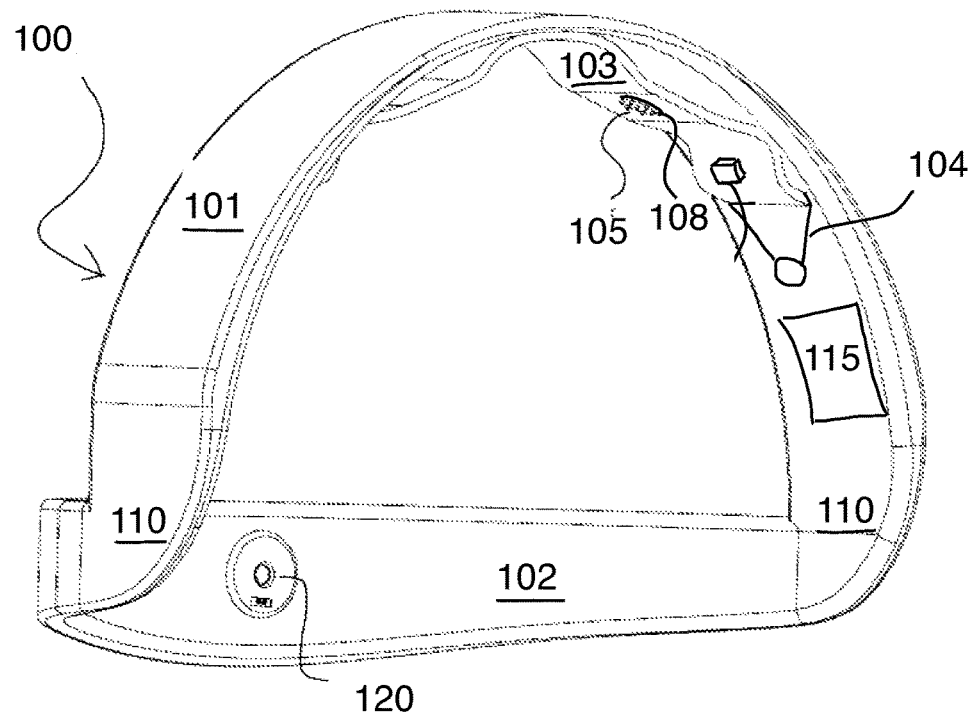
FIG. 1 illustrates an embodiment of the disclosed invention.

Referring to FIG. 1, one embodiment of the disclosed invention comprises an EEG monitor 100 with at least sensors 105 to detect brain waves. The brain emits theta waves from the temporal lobe and alpha waves from the occipital and parietal lobes. The sensors 105 are placed to optimize reception of the signals. The desired frequency of activation is below 12 Hz, especially between 3 Hz and 8 Hz or the range of 4 Hz to 7 Hz. The detected brain wave signals are transmitted to a microprocessor which analyzes the signals and determines the brain waves being detected. These transmissions by be wired or wireless transmissions. The brain waves are continuously monitored and the data is continuously transmitted to a microprocessor for processing in intervals ranging from once every 0.01 milliseconds to once every second or longer, and preferably once every 20 milliseconds. If brain waves are detected in a predetermined range, such as below 12 Hz, or between 3 Hz and 8 Hz, then the microprocessor activates a stimulus 120, which may be visual, auditory or tactile, such as an actuator, a phone call or any other stimulus to stimulate the brain change the waves being transmitted by it.

Figure 2A:
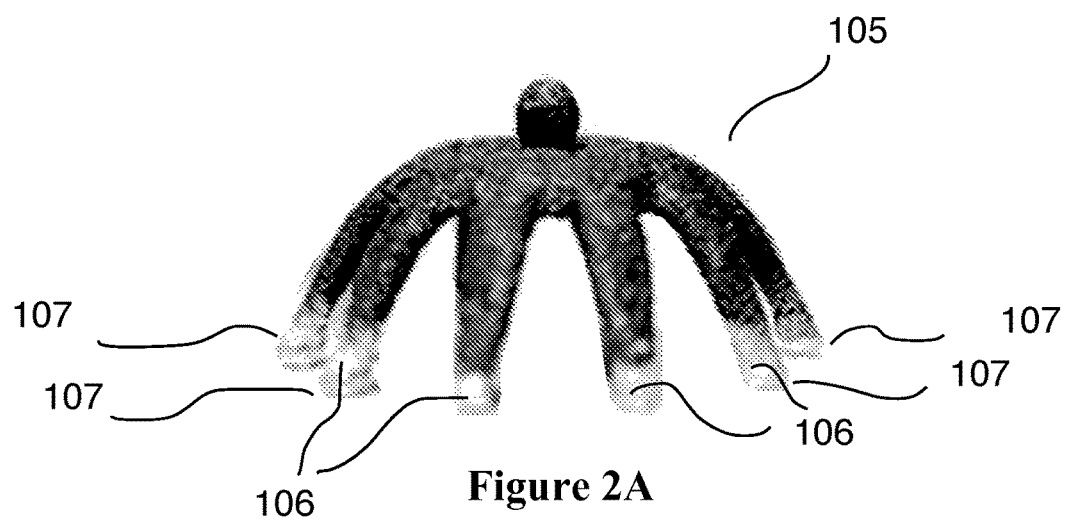
FIG. 2A illustrates an embodiment of a sensor.
Figure 2B:
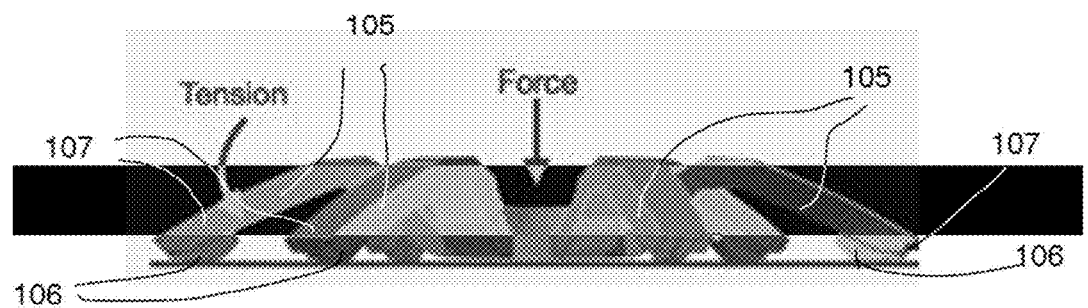
FIG. 2B illustrates an alternative view of a sensor.
Figure 2C:
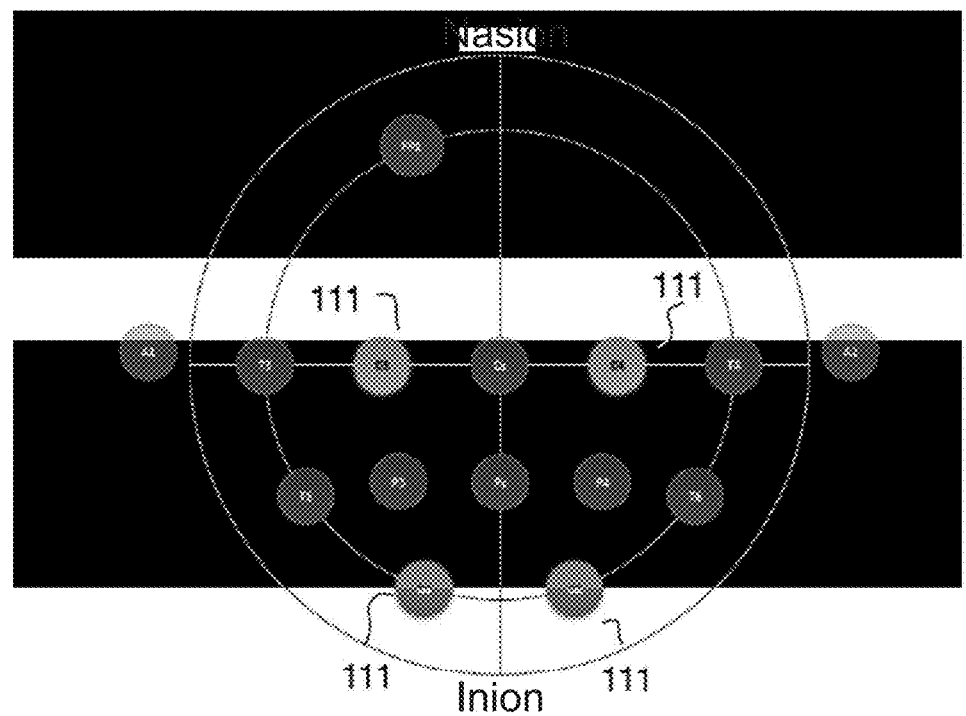
FIG. 2C illustrates a map of the international 10-20 system for potential sensor placements.

Referring now to FIGS. 2A-2C, the sensor 105 may comprise any EEG sensors known in the art. The sensors may be wet or dry sensors. The sensors may be made from metal, plastic, composite or any other materials. The sensors 105 may comprise silver chloride on the tips 106 to reduce impedance and improve conductance. The sensors may comprise conductive fabrics, plastics or metals. In certain embodiments the disclosed invention inputs signals from a reference sensor and EEG sensors into an op amp, which runs the signal through a series of low-pass filters and outputs to a stimulus 120. The power supply may comprise 6V provided by external batteries. The stimulus is customizable and can range from an audible buzzer to a vibrator motor.

The sensors 105 may be dry EEG electrodes composed of mostly silver alloy. The device may be analog and without a need to use an analog to digital converter. All sensors 105 and electronics are incorporated into a headwear piece that can be customized according to the user's style.

In a preferred embodiment a dry sensor 105 manufactured by COGNIONICS, is used. The sensor 105 is designed to brush through hair with modest pressure while retaining the ability to flatten for safety and comfort is used. (See FIG. 2B). When a force is applied to the top of the sensor 105 the sensor flattens and the legs 107 of the sensor 105 are under tension, increasing the pressure between the end of the legs and the scalp. The pressure improves the contact between the sensor 105 and the scalp. Moreover, as the leg 107 is flexed the tip of the leg pushes obstructions, such as hair, out of the way to allow the sensor 105 to directly contact the scalp. The tips of the legs 107 may be coated with materials to improve the sensor's ability to detect brain waves. One coating may be silver chloride 106. The spider-style sensor is used in connection with hair on a scalp and the tips of the "spider" legs extend through the subject's hair to directly contact the scalp.

Figure 3A:
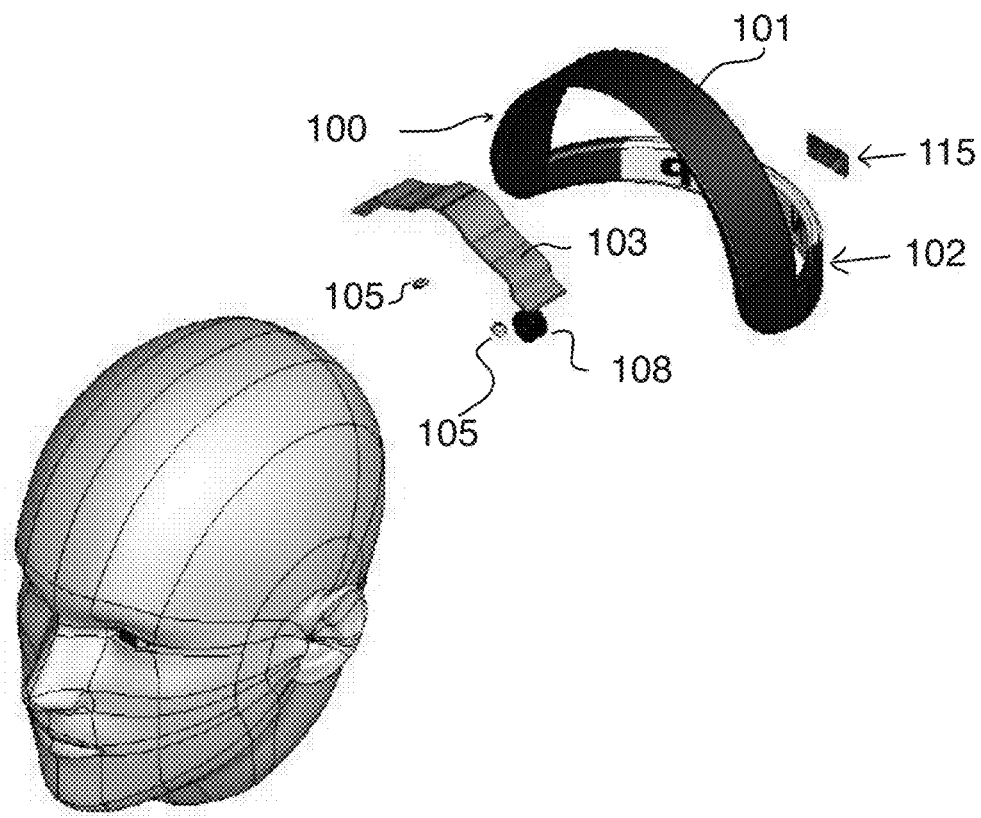
FIG. 3A illustrates an exploded view of an embodiment of the disclosed invention.
Figure 3B:
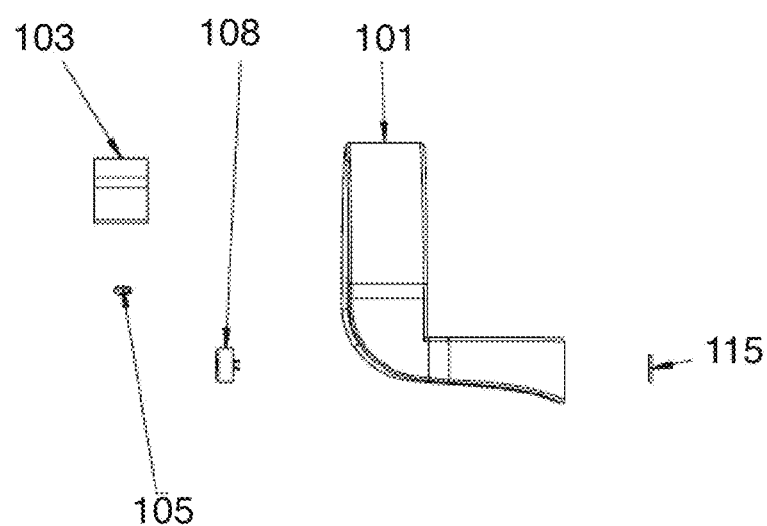
FIG. 3B illustrates parts of an embodiment of the disclosed invention.

Referring to FIGS. 1, 3A and 3B, the sensors may be held in place by an EEG sensor 100. The EEG sensor 100 apparatus may comprise a frame, or an article of clothing, such as a hat, a visor, a bandana, a skull cap, a ski hat, headband, or any other article which can position the sensors in place. In alternative embodiments the harness apparatus may comprise clips which clip the sensors to hair.

In a preferred embodiment the harness apparatus is a two-part harness with a headband portion 101 that extends across the crown of the scalp and a base portion 102 which extends around the rear base of the head. The headband portion 101 is a semi-rigid member comprising extendable sizing members to allow the length of the headband to be selectively adjusted. At least two sensors 105 are selectively coupled to the headband at least some distance apart such as 1 centimeter apart. However, in a preferred embodiment there are four sensors spaced on the headband portion 101 to be spread across the scalp so as to be optimally positioned to detect theta waves generated by the brain. In the preferred embodiment width of the headband 101 is sufficient to allow the four sensors 105 to be placed within ten percent of the C3, C4 O1 and O2 111 (see FIG. 2C) locations as determined by the 10-20 electrode placement system, allowing the sensors to be optimally located to detect theta waves being emitted from the occipital and parietal lobes of the brain.

The sensors 105 may be positioned on the scalp or placed on the scalp. Placement of the sensors 105 is based on the optimal location (FIG. 2C) necessary to detect and properly acquire the brain waves and obtain an EEG reading. The sensors may be placed according to the international 10-20 system at areas C3, C4, O1, and O2 111. Each point on this system can represent between 10 and 20 percent of the total skull region. Alternative embodiments may comprise placing the sensors in alternative locations on the scalp for additional scoring channels and/or derivations. Areas A1, A2, F7, F8, Fp1, and Fp2 may be used for ambient frequency references. Area Fp1 and Fp2 above the left and right canthi may be used for electro-oculogram recordings.

In certain embodiments a nested frame 103 nests inside the concave surface of the headband portion 101. The frame 103 may be made of any material, and in preferred embodiments the frame 103 is compliant and made of silicone, rubber or other materials that comfortably takes the contoured shape of the person's head who is wearing the monitor 100. The frame 103 is coupled to the headband portion by adjustable members 104, which may comprise elastomeric members to allow the pressure applied by the compliant frame to the head is constant and adjustable. The adjustable members 104 may also comprise slide mechanisms, hook and loop system, peg and hole system, or any other mechanism or system that allows for selectively securing the nested frame 103 at the desired position.

The frame 103 may further comprise sensors 105 selectively coupled to the compliant frame. In certain embodiments foam spacers 108 may also be coupled to the frame 103. The spacer may be doughnut-shaped and surround the sensor 105 with the sensor sitting in the center of the doughnut hold. Alternatively the foam spacer may be coupled to the compliant frame some distance from the sensor to keep the applied pressure even across the subject's scalp or head. In both embodiments where the foam spacer surrounds the sensor or where the foam spacer is off-set from the senor, the foam is approximately the same height as the senor. In certain embodiments the foam is lightly less than the height of the sensor. In other embodiments the height of the foam is slightly less than the height of the senor.

The terminal ends of the headband comprise nodes 110 which couple the headband portion 101 to the base portion 102. The node 110 is adjustable and allows the angle between the base portion 102 and the headband portion 101 to increase or decrease as needed to place properly place the sensors. The base portion 102 extends around the base of the skull. The base portion may comprise an stimulator 120. The base portion stimulator 120 may stimulate visual, auditory or tactile senses. In a preferred embodiment the stimulator 120 vibrates and is positioned at the center base of the skull to stimulate thalamus, the brain structure responsible for sleep.

The sensors 105 are in communication with a microprocessor 115 which analyzes signals detected by the sensors 105 to determine if the detected brain waves are within the predetermined frequency range.

Figure 4A:
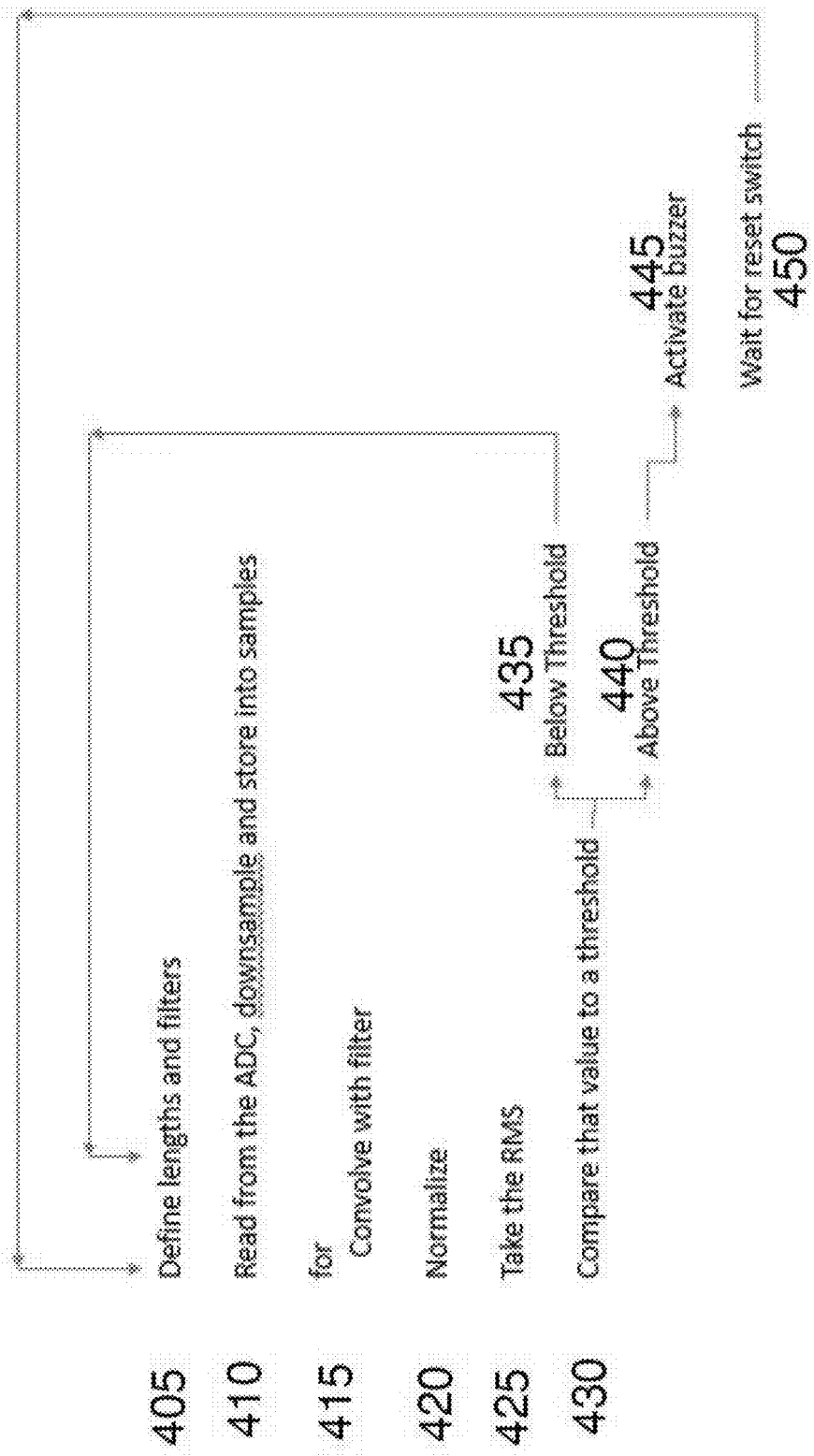
FIG. 4A illustrates a flow diagram of an embodiment of the disclosed invention.
Figure 4B:
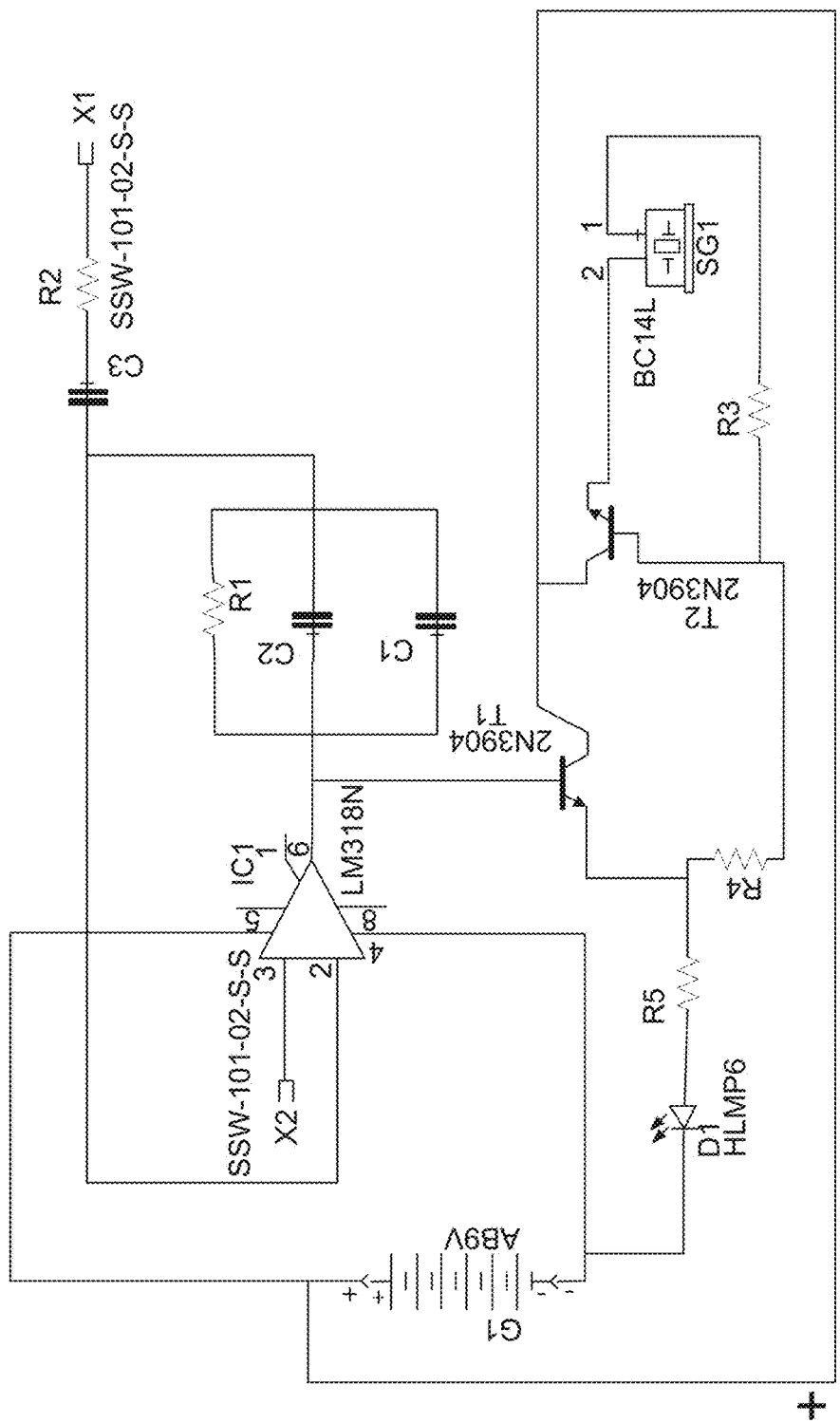
FIG. 4B illustrates a circuit an embodiment of the disclosed invention.
Figure 4C:
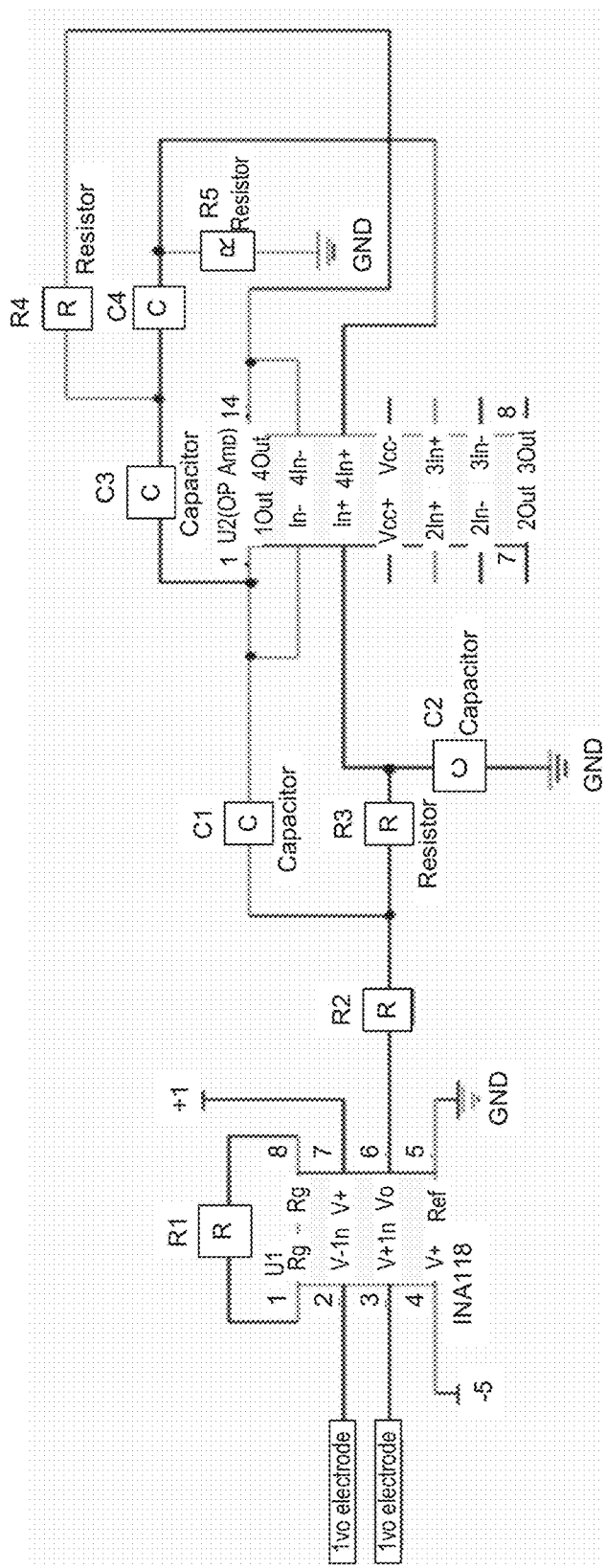
FIG. 4C illustrates a circuit an alternative embodiment of the disclosed invention.
Figure 5:
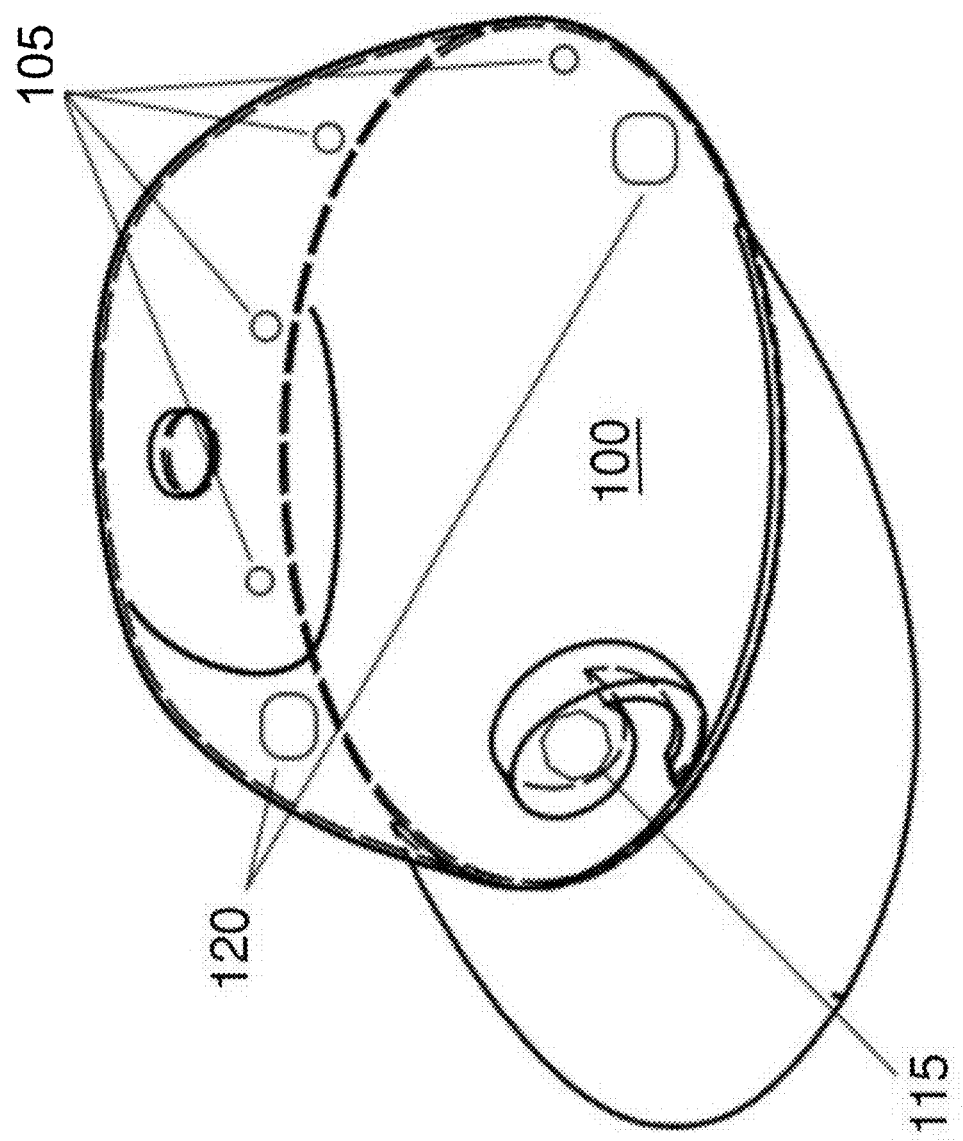
FIG. 5 illustrates an alternative embodiment of the disclosed invention.

Referring to FIGS. 4A-4C, an electrical circuit is created for sensing and transmitting brain signals to a microprocessor 115. The signals from the brain are detected by sensors 105 placed on the scalp. A minimum of two sensors a minimum distance apart are needed to detect the signals. In addition, a reference value is required as well as a circuit ground. The reference provides a reference from which all other sensors are differentiated, and another sensor to provide a point from which to differentiate. The reference to ground sensor can be separated into a ground sensor and a reference sensor. The reference sensor can be of any conductive material and can be placed anywhere on the head. The reference sensor may be constantly detecting a signal, or alternatively, it may be a baseline value gathered through an initial reading and then stored in the invention's logic to obtain differentials. The reference's function is to provide a differential reference point to measure brain wave attributes. The ground sensor can be of any conductive material and can be placed anywhere on the body. Its function is an electric ground of the body. A preferred embodiment uses six sensors: one reference, one ground, and four additional sensors at C3, C4, O1, and O2 111 to pinpoint theta wave readings. The ground and reference are pad sensors, and are placed on the bare scalp. The other four sensors are spider-like flexible sensors 105 that are designed to measure through hair and still make contact with the scalp. (Both bought from COGNIONICS). The headband 101 apparatus ensures correct sensor placement and pressure is used. The headband apparatus 101 may include rigid and elastic parts to maintain pressure and comfort of the sensors against the head. The headband apparatus 101 can either fit inside or be integrated into existing headwear. The apparatus may be adjustable. Processing unit and additional circuitry may be housed within the apparatus.

In addition, impedance values and placement of the sensors are used to determine sensing accuracy of the invention. Thus if a sensor's impedence is high, and a signal is not being detected, then the microprocessor will generate a signal, such as the stimulator 120, or a message, such as a text message to an off-site location to notify the system is gathering data and the subject's wakefulness state. The invention will determine when sensing accuracy is within a desired range and notify the user. Notification may occur with audible, optical, or other methods. The invention may also notify the user if sensing accuracy is not within desired range using any of the same methods.

The signals are detected by sensors 105 and go through a filtering circuit which may include various amplifying circuitry, anti-aliasing filters, analog digital converters, a microprocessor, power supply, and waking mechanism. The signal noise may be reduced or eliminated by any of the aforementioned devices. The microcontroller processes the signal as follows: Algorithm defines time and size of data packets 405. The signals are read from the analog digital converter 410, down-sampled based on means 410, and stored into samples 410. The samples go into a "for" loop which includes a convolution with filtering coefficients 415, normalization 420, taking the root mean square 425, and comparing that value to a threshold 430. Once the value exceeds the threshold, the stimulator is activated 445. The stimulator 120 may require user input to reset to loop 450. If threshold is not reached 435, the "for" loop continues until it is reached. The algorithm is designed to activate once theta waves indicate microsleep or drowsiness. The algorithm may include a time-based or packet-counter based recognition function.

The stimulator 120 may include, but is not limited to an audible buzzer, a vibrating buzzer, an electric pulse, a low pulse frequency to stimulate the thalamus, a phone call, a mobile app-related action, shutting off of equipment, a magnetic pulse, or a notification via text or by push notification. Data may be recorded by a central monitoring station, if applicable.

The device may also be used to help people with sleep disorders monitor their conscious states. Applications and markets for the invention may include, but are not limited to, transportation industries, national security, police departments, manufacturing facilities, software industries, medical industries, marketing industries, call centers, educational institutions, religious institutions, consumer driving, studying, and alerting in any situation.

What is claimed:

1. A brain wave monitoring apparatus, comprising:
   headgear configured to be secured to a head of a user;
   a microprocessor coupled to the headgear;
   a plurality of sensors in communication with the microprocessor and coupled to the headgear, wherein the plurality of sensors are configured to detect brain waves emitted from a brain of the user and output signals indicative of the detected brain waves; and
   a stimulator coupled to the headgear;
   wherein the microprocessor is configured to receive and filter the signals output from the plurality of sensors based on wave frequency to determine when to output a stimulus signal, wherein the microprocessor is configured to:
   read analog signals from the sensors;
   convert the analog signals to digital signals using based on an analog to digital converter;
   down-sample the digital signals based on a mean value to packets;
   store the packets into samples;
   place the samples in a logic loop which includes a convolution with filtering coefficients assigned to the samples based on wave frequency;
   normalize the samples; and
   take the root mean square of the normalized samples to create data packets;
   run the data packets through a packet-counter based recognition function wherein signal waves in a range of 3 Hz to 8 Hz are assigned a first filtering coefficient value and counted and signal waves in a range of greater than 8 Hz to less than 12 Hz are assigned a second filtering coefficient value and counted, wherein the first value and the second value are combined to create a packet-counter based recognition function value; and determine when to output a stimulus signal based on a comparison of the packet-counter based recognition function value indicative of the signals to a threshold value such that when the microprocessor determines that the packet-counter based recognition function value exceeds the threshold value, the microprocessor outputs a stimulus signal to the stimulator causing the stimulator to provide a visual, auditory, or tactile stimulus to the user.

2. The apparatus of claim 1 wherein the sensors further comprise dry-contact sensors.

3. The apparatus of claim 1, wherein the stimulator is positioned at a center base of the head when the headgear is secured to the head of the user.

4. The apparatus of claim 1, wherein the plurality of sensors are spaced laterally across a crown of the head.

5. A brain wave monitoring apparatus, comprising
headgear configured to be secured to a head of a user;
a microprocessor coupled to the headgear;
a plurality of sensors in communication with the microprocessor and coupled to the headgear, wherein the plurality of sensors are configured to detect brain waves emitted from a brain of the user and output signals indicative of the detected brain waves; and
a stimulator coupled to the headgear;
wherein the microprocessor is configured to:
define a time interval and data size of data packets;
read signals from an analog to digital converter and place the signals in the data packets;
down-sample the signals;
store samples of the signals in the microprocessor;
pass the samples through a "for" loop that includes a convolution with filtering coefficients;
normalize the samples;
take the root mean square of the normalized samples to obtain a root mean square value;
run the root mean square value through a packet-counter based recognition function wherein signal waves from 3 Hz to 8 Hz are counted to create a first filtering coefficient value and signal waves from greater than 8 Hz to less than 12 Hz are counted to create a second filtering coefficient value, wherein the sum of the first value and the second value comprise the packet-counter based recognition function value;
compare the packet-counter based recognition function value to a threshold value; and
determine whether the packet-counter based recognition function value exceeds the threshold value, such that in response to the microprocessor determining that the packet-counter based recognition function value exceeds the threshold value, the microprocessor outputs a stimulus signal to the stimulator causing the stimulator to provide a visual, auditory, or tactile stimulus to the user.

6. The apparatus of claim 5, wherein the signals are between 3 and 8 Hz.

7. The apparatus of claim 5, wherein the stimulator is positioned at a center base of the head when the headgear is secured to the head of the user.

8. The apparatus of claim 5, wherein the stimulus includes a tactile vibration.

9. The apparatus of claim 5, wherein the stimulus includes an electric pulse.

10. The apparatus of claim 5, wherein the plurality of sensors are spaced laterally across a crown of the head.

11. The apparatus of claim 5, wherein the signals are indicative of the detected brain waves corresponding to the brain transitioning from an alert state to a sleep state.

12. The apparatus of claim 5, further comprising a user-operated switch configured to reset the "for" loop.

13. A brain wave monitoring apparatus, comprising:
headgear comprising a plurality of brain wave sensors configured to detect analog brain waves;
a stimulator; and
a microprocessor configured to:
read analog signals from the sensors;
convert the analog signals to digital signals using an analog to digital converter;
down-sample the digital signals based on a mean value to packets;
store the packets into samples;
place the samples in a logic loop which includes a convolution, wherein a first filtering coefficient value is assigned to signal waves in the range of between 3 Hz to 8 Hz and a second filtering coefficient value is assigned to signal waves in the range of between 8 Hz and 12 Hz;
normalize the samples;
take the root mean square of the normalization to create data packets;
run the data packets through a packet-counter based recognition function wherein the samples having a first filtering coefficient value and the samples having a second filtering coefficient value are combined to constitute a packet-counter based recognition function value; and
determine when to output a stimulus signal based on comparison of the packet-counter based recognition function value indicative of the signals to a threshold value such that when the microprocessor determines that the packet-counter based recognition function value exceeds the threshold value the microprocessor outputs a stimulus signal to the stimulator causing the stimulator to provide a visual, auditory, or tactile stimulus to the user.

* * * * *